(12) United States Patent
Wheeler

(10) Patent No.: US 8,377,028 B2
(45) Date of Patent: Feb. 19, 2013

(54) PROCESS FOR MAKING A PANT-LIKE DISPOSABLE ABSORBENT GARMENT HAVING AN UNDERWEAR-LIKE WAISTBAND GRAPHIC, AND GARMENT MADE THEREBY

(75) Inventor: Katherine C. Wheeler, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 573 days.

(21) Appl. No.: 12/470,309

(22) Filed: May 21, 2009

(65) Prior Publication Data

US 2010/0298799 A1  Nov. 25, 2010

(51) Int. Cl.
*A61F 13/15* (2006.01)

(52) U.S. Cl. .............. 604/396; 604/385.24; 604/385.25; 604/385.27; 156/160; 156/163

(58) Field of Classification Search ............ 604/385.01, 604/385.24, 385.25, 385.26, 385.27, 396; 156/160, 163
See application file for complete search history.

(56) References Cited

U.S. PATENT DOCUMENTS

| | | |
|---|---|---|
| D257,884 S | 1/1981 | Ternstrom |
| D281,540 S | 12/1985 | Ternstrom |
| D284,036 S | 6/1986 | Birring |
| D334,619 S | 4/1993 | Barraza |
| 5,224,405 A | 7/1993 | Pohjola |
| 5,358,500 A | 10/1994 | Lavon et al. |
| 5,458,590 A | 10/1995 | Schleinz et al. |
| 5,503,076 A | 4/1996 | Yeo |
| 5,545,158 A | 8/1996 | Jessup |
| 5,591,151 A | 1/1997 | Hasse et al. |
| 5,612,118 A | 3/1997 | Schleinz et al. |
| D382,054 S | 8/1997 | Berdichevsky |
| 5,766,389 A | 6/1998 | Brandon et al. |
| D422,077 S | 3/2000 | Suprise et al. |
| D422,078 S | 3/2000 | Vukos et al. |
| D438,304 S | 2/2001 | Popp et al. |
| D438,614 S | 3/2001 | Ratliff et al. |
| D438,615 S | 3/2001 | Dimitrijevs et al. |
| D439,662 S | 3/2001 | Ratliff et al. |
| D477,872 S | 7/2003 | Sosalla |
| 6,723,034 B2 | 4/2004 | Durrance et al. |
| 6,733,483 B2 | 5/2004 | Raufman et al. |
| D492,409 S | 6/2004 | Otsubo et al. |
| 6,764,475 B1 | 7/2004 | Olson |
| 6,849,067 B2 | 2/2005 | Fletcher et al. |
| D522,653 S | 6/2006 | Otsubo et al. |

(Continued)

FOREIGN PATENT DOCUMENTS

| WO | WO 01/49230 A1 | 7/2001 |
|---|---|---|
| WO | WO 2007/024327 A1 | 3/2007 |

*Primary Examiner* — Jacqueline F. Stephens
(74) *Attorney, Agent, or Firm* — R. Joseph Foster, III; H. Michael Kubicki

(57) ABSTRACT

A process for making a pant-like disposable absorbent garment comprising: providing a front panel and back panels and an absorbent insert which extends between the front and back panels; printing a front waistband graphic on the front panel such that the front waistband graphic extends at least 90% of the front panel width; printing a back waistband graphic on the back panel such that the back waistband graphic extends at least 90% of the back panel width; and joining the first and second front side edges to the first and second back side edges, such that the garment assumes a pull-on configuration, and such that the front waistband graphic is in at least substantial alignment with the back waistband graphic. A garment made by the process is also disclosed.

19 Claims, 12 Drawing Sheets

U.S. PATENT DOCUMENTS

| | | |
|---|---|---|
| 7,107,621 B2 | 9/2006 | Meekins |
| 7,178,571 B2 | 2/2007 | Vergona |
| D541,008 S | 4/2007 | Fairhurst et al. |
| 7,270,651 B2 | 9/2007 | Adams et al. |
| 7,306,582 B2 | 12/2007 | Adams et al. |
| 7,311,696 B2 | 12/2007 | Christon et al. |
| D573,254 S | 7/2008 | Kawakami et al. |
| 7,402,157 B2 | 7/2008 | Christon et al. |
| D574,489 S | 8/2008 | Kawakami et al. |
| D577,119 S | 9/2008 | Kawakami et al. |
| 7,432,413 B2 | 10/2008 | Roe et al. |
| D583,935 S | 12/2008 | Sasayama et al. |
| D583,936 S | 12/2008 | Sasayama et al. |
| D591,421 S | 4/2009 | Kawakami et al. |
| 7,520,873 B2 | 4/2009 | Sosalla et al. |
| 7,537,585 B2 | 5/2009 | Christon et al. |
| 2002/0062117 A1 | 5/2002 | Raufman et al. |
| 2003/0114811 A1 | 6/2003 | Christon et al. |
| 2004/0019343 A1 | 1/2004 | Olson et al. |
| 2004/0028268 A1 | 2/2004 | Popp et al. |
| 2004/0122398 A1 | 6/2004 | Schnabel et al. |
| 2005/0015066 A1 | 1/2005 | Anderson et al. |
| 2005/0143698 A1 | 6/2005 | Sosalla et al. |
| 2005/0148961 A1 | 7/2005 | Sosalla et al. |
| 2005/0177120 A1 | 8/2005 | Olson et al. |
| 2006/0004333 A1 | 1/2006 | Olson |
| 2006/0020249 A1 | 1/2006 | Allen |
| 2006/0021536 A1 | 2/2006 | Song et al. |
| 2007/0049889 A1 | 3/2007 | Larson et al. |
| 2007/0095234 A1 | 5/2007 | Hopman |
| 2007/0208318 A1 | 9/2007 | Loritz et al. |
| 2007/0250023 A1 | 10/2007 | Strannemalm |
| 2008/0013872 A1 | 1/2008 | Geiger |
| 2008/0108967 A1 | 5/2008 | Mizushima et al. |
| 2008/0132872 A1 | 6/2008 | Trennepohl et al. |
| 2009/0197041 A1 | 8/2009 | Lake et al. |

PROCESS FOR MAKING A PANT-LIKE DISPOSABLE ABSORBENT GARMENT HAVING AN UNDERWEAR-LIKE WAISTBAND GRAPHIC, AND GARMENT MADE THEREBY

BACKGROUND

Pant-like disposable absorbent garments are in common use in today's society. For example, disposable absorbent underwear for incontinence and enuresis conditions, disposable training pants, and disposable menstrual panties are common in the marketplace. It is desirable to make such products as much like normal cloth underwear as possible. For example, wearers of incontinence and enuresis garments generally wish to conceal the fact that they are wearing such products, and therefore desire the garments to resemble normal cloth underwear as closely as possible. In another example, children wearing training pants take pride in the fact that they are no longer wearing diapers, and providing them with a disposable training pant product that closely resembles real underwear supports this process. Pant-like disposable garments currently on the market have additional room for optimization in terms of better resembling normal cloth underwear. Additionally, there remains a need for an improved method of making pant-like disposable absorbent garments that better resemble normal cloth underwear.

SUMMARY OF THE INVENTION

To meet the above-described unmet needs in the art, a new process for making a pant-like disposable absorbent garment having an underwear-like waistband graphic, and a garment made thereby, have been invented.

In one aspect, the present invention relates to a process for making a pant-like disposable absorbent garment comprising: providing a front panel, the front panel defining a front waist edge, first and second front leg edges, opposing first and second front side edges which extend from the front waist edge to the first and second front leg edges, and a front panel width which extends from the first front side edge to the second front side edge at the front waist edge; providing a back panel, the back panel defining a back waist edge, first and second back leg edges, opposing first and second back side edges which extend from the back waist edge to the first and second back leg edges, and a back panel width which extends from the first back side edge to the second back side edge at the back waist edge; attaching an absorbent insert to the front panel and to the back panel, such that the absorbent insert extends between and connects the front panel to the back panel; printing a front waistband graphic on the front panel proximate the front waist edge, such that the front waistband graphic extends at least 90% of the front panel width; printing a back waistband graphic on the back panel proximate the back waist edge, such that the back waistband graphic extends at least 90% of the back panel width; and joining the first and second front side edges to the first and second back side edges, such that the garment assumes a pull-on configuration, and such that the front waistband graphic is in at least substantial alignment with the back waistband graphic. In particular embodiments, the joining of the first and second front side edges to the first and second back side edges places the front waistband graphic in complete alignment with the back waistband graphic.

In another aspect, the present invention relates to a pant-like disposable absorbent garment comprising: a front panel, the front panel defining a front waist edge, first and second front leg edges, opposing first and second front side edges which extend from the front waist edge to the first and second front leg edges, and a front panel width which extends from the first front side edge to the second front side edge at the front waist edge; a back panel, the back panel defining a back waist edge, first and second back leg edges, opposing first and second back side edges which extend from the back waist edge to the first and second back leg edges, and a back panel width which extends from the first back side edge to the second back side edge at the back waist edge, the first and second front side edges being joined to the first and second back side edges such that the garment defines a pull-on configuration; an absorbent insert extending between and interconnecting the front panel to the back panel; a front waistband graphic disposed on the front panel proximate the front waist edge, the front waistband graphic extending at least 90% of the front panel width; and a back waistband graphic disposed on the back panel proximate the back waist edge, the back waistband graphic extending at least 90% of the back panel width, wherein the front waistband graphic is in at least substantial alignment with the back waistband graphic. In particular embodiments, the front waistband graphic is in complete alignment with the back waistband graphic. In particular embodiments, the garment defines a waist hoop, and the front waistband graphic and the back waistband graphic together define a garment waistband graphic that extends around an entire circumference of the waist hoop.

DETAILED DESCRIPTION OF EXEMPLARY EMBODIMENTS

Figure 1:
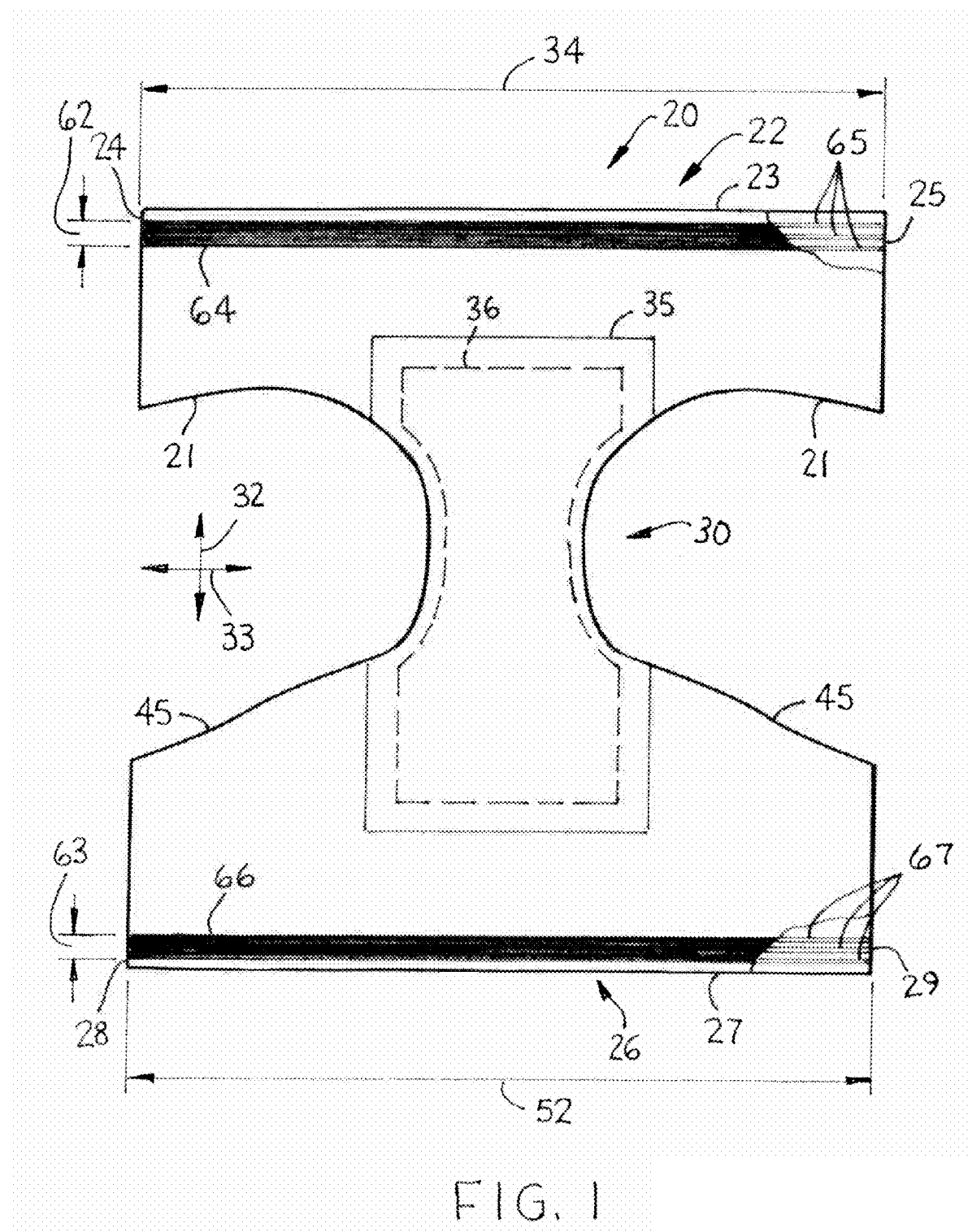
FIG. 1 representatively illustrates a plan view of one embodiment of an absorbent garment incorporating principles of the garment aspect of the present invention in a longitudinally stretched and laid-flat condition, prior to the joining of the front and back waist regions, and showing the surface of the article that faces the wearer when the article is worn, and with portions cut away to show underlying features.

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

A description of exemplary embodiments of the process and garment aspects of the present invention shall now be presented. Examples of the pant-like disposable absorbent garment are adult incontinence absorbent underwear, youth absorbent enuresis pants, children's absorbent training pants, absorbent menstrual panties, and the like.

Referring to FIGS. 1-15, which illustrate exemplary embodiments of the invention, a process for making a pant-like disposable absorbent garment comprises providing a front panel 22, the front panel 22 defining a front waist edge 23, first and second front leg edges 21, opposing first and second front side edges 24 and 25 which extend from the front waist edge 23 to the first and second front leg edges 21, and a front panel width 34 which extends from the first front side edge 24 to the second front side edge 25 (as measured at the front waist edge when the product is in a laid-flat, open, and fully extended configuration). The process further includes providing a back panel 26, the back panel 26 defining a back waist edge 27, first and second back leg edges 45, opposing first and second back side edges 28 and 29 which extend from the back waist edge 27 to the first and second back leg edges 45, and a back panel width 52 which extends from the first back side edge 28 to the second back side edge 29 (as measured at the back waist edge when the product is in a laid-flat, open and fully extended configuration).

Figure 2:
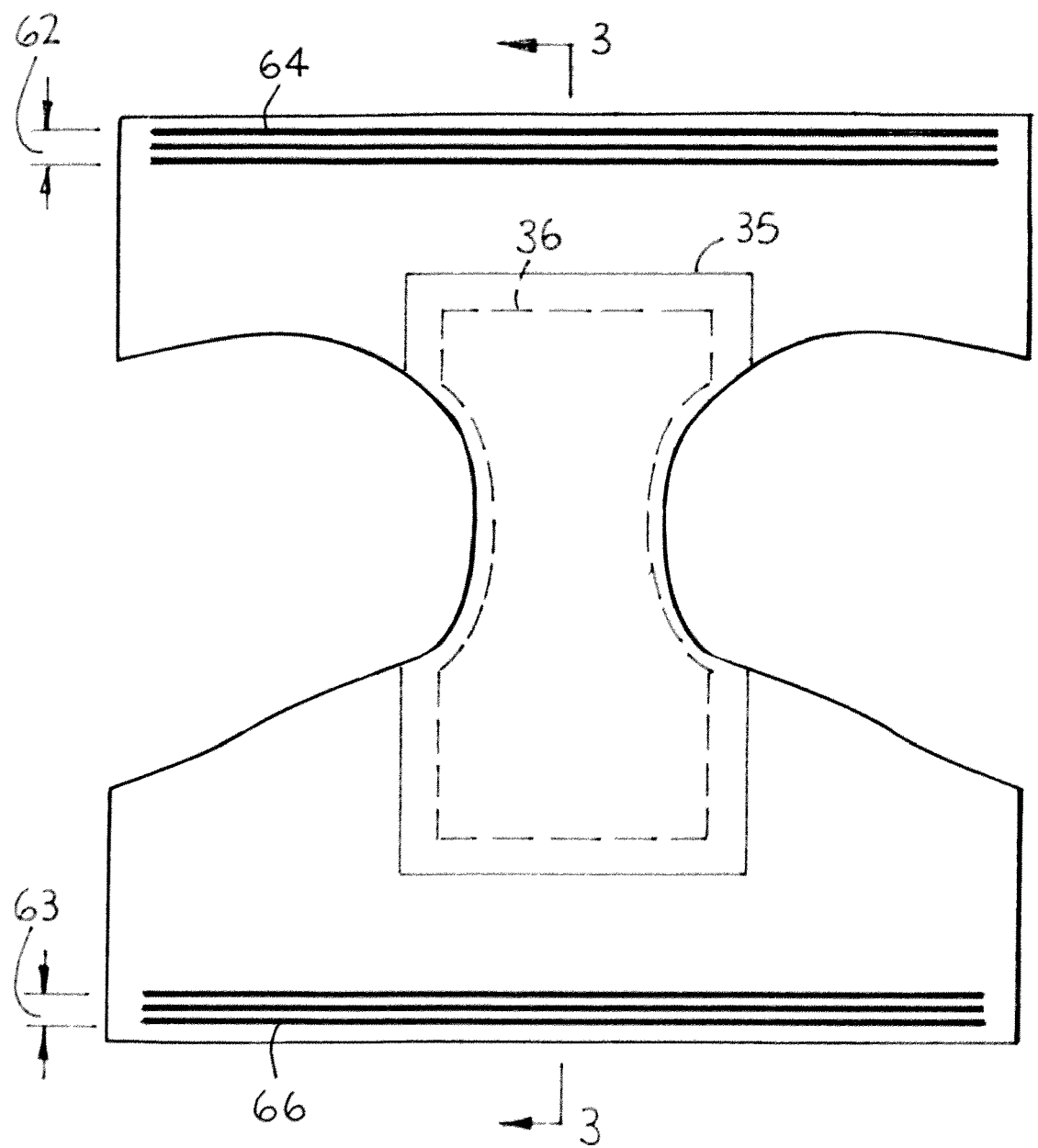
FIG. 2 representatively illustrates an alternative embodiment of the garment of FIG. 1.
Figure 3:
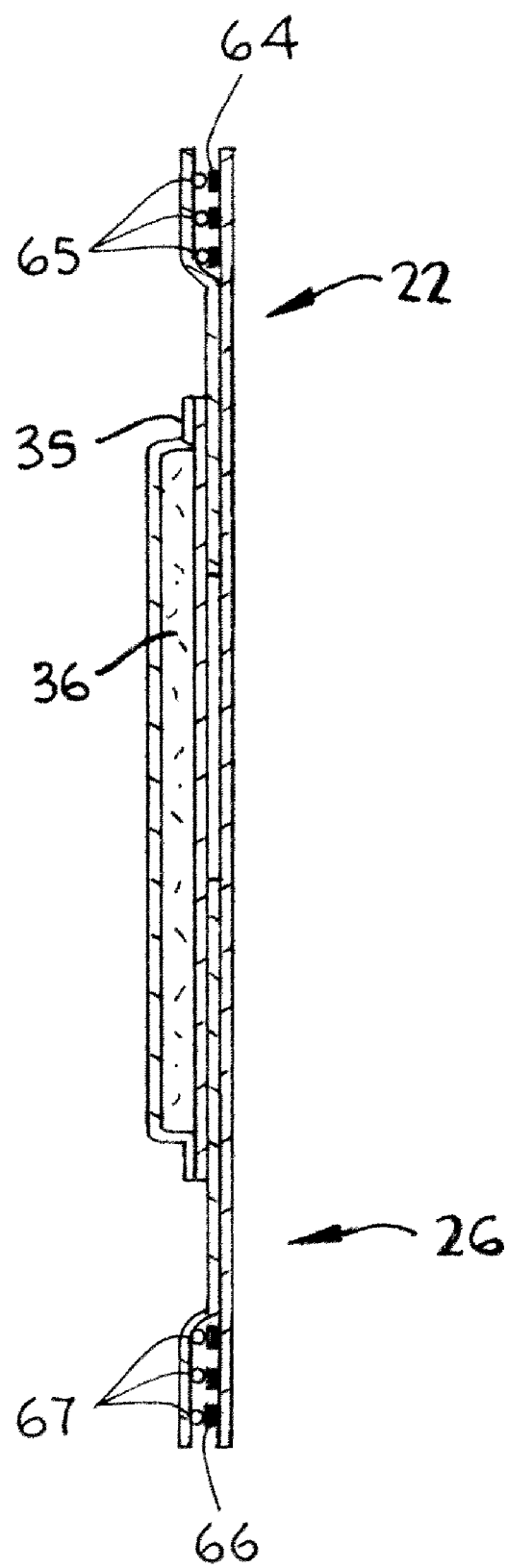
FIG. 3 representatively illustrates a cross-sectional view of the garment of FIG. 2 taken along line 3-3.
Figure 12:
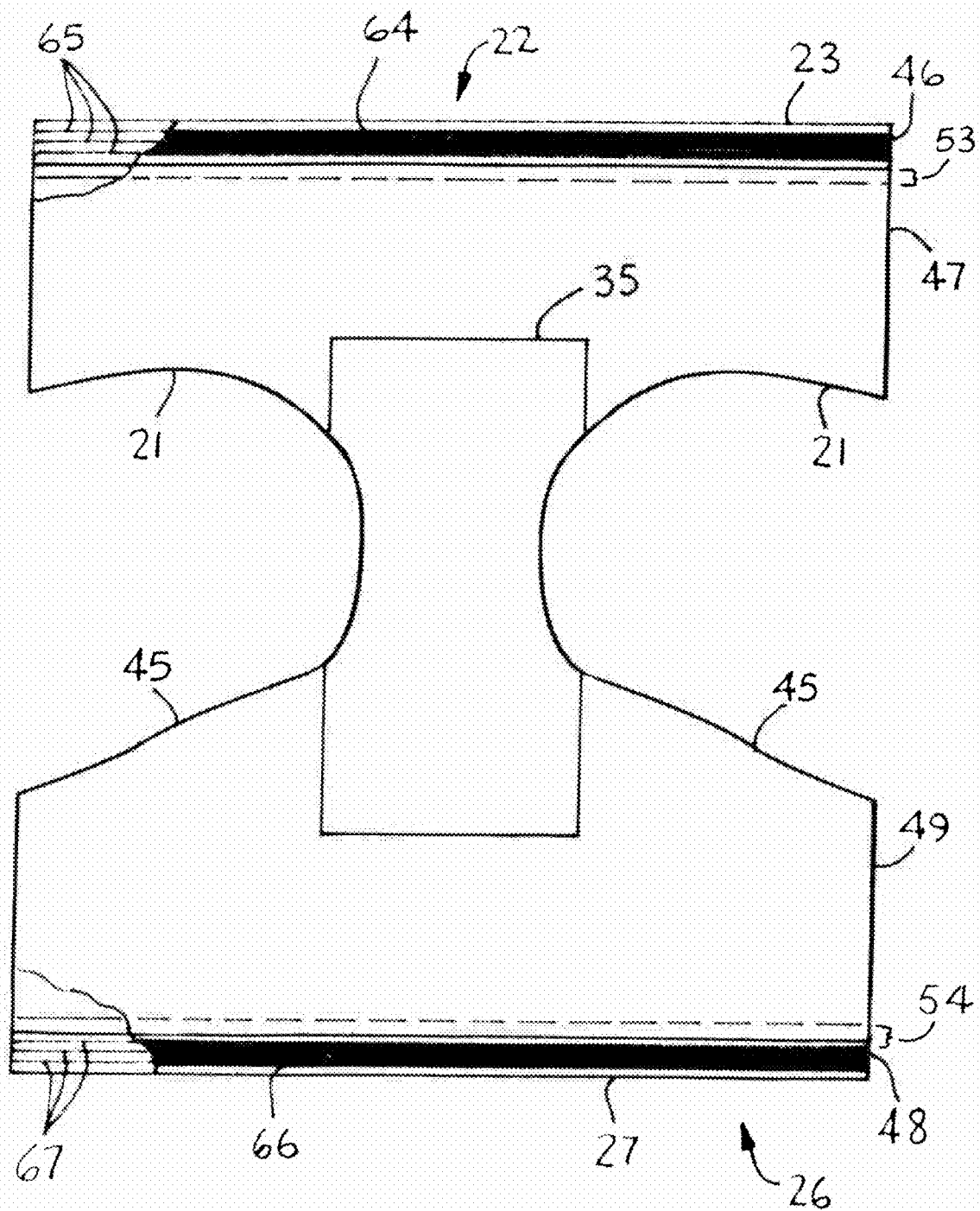
FIG. 12 representatively illustrates a plan view of an alternative embodiment of an absorbent garment incorporating principles of the garment aspect of the present invention in a longitudinally stretched and laid-flat condition, prior to the joining of the front and back waist regions, and showing the surface of the article that faces the wearer when the article is worn.
Figure 13:
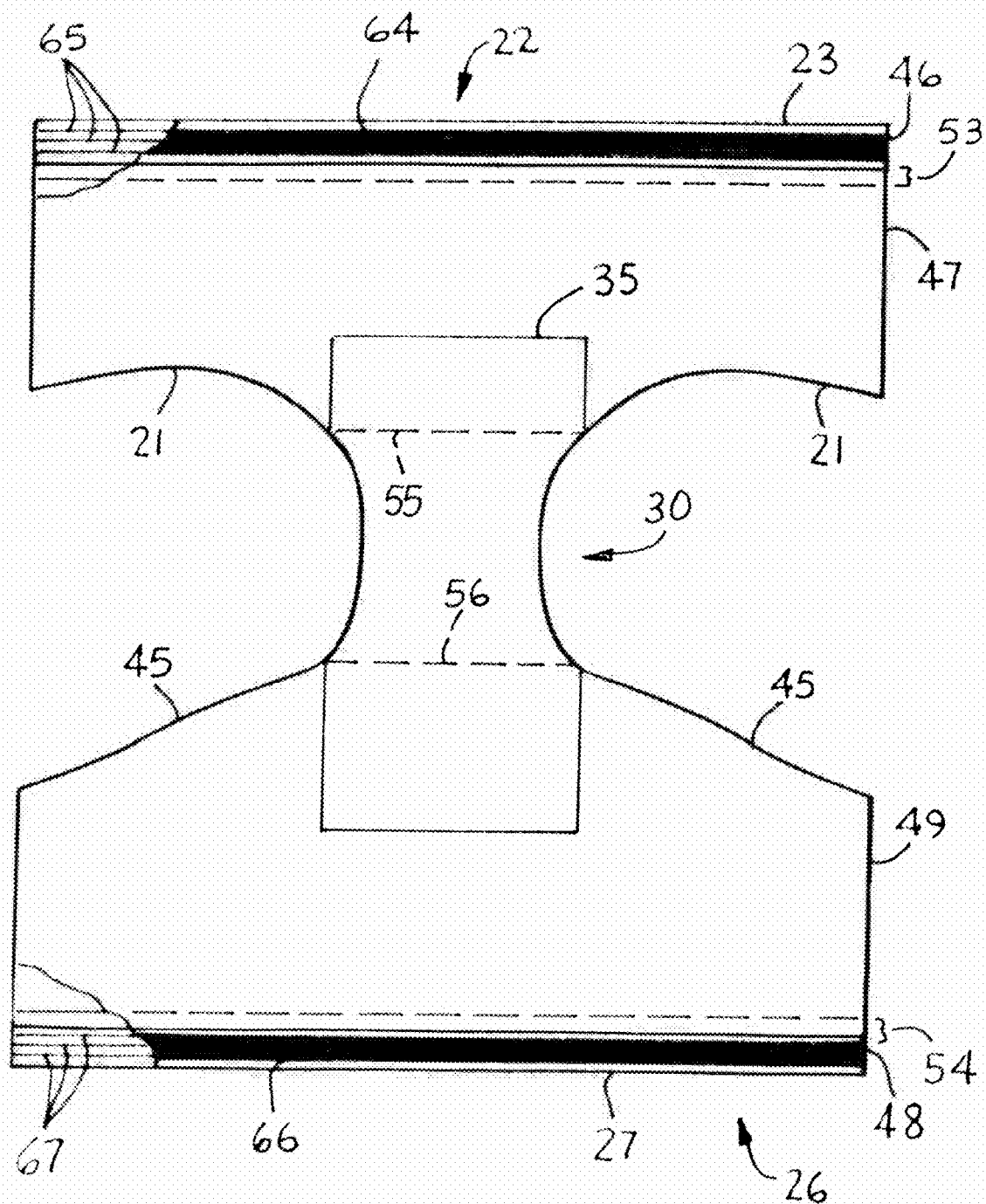
FIG. 13 representatively illustrates a plan view of an alternative embodiment of an absorbent garment incorporating principles of the garment aspect of the present invention in a longitudinally stretched and laid-flat condition, prior to the joining of the front and back waist regions, and showing the surface of the article that faces the wearer when the article is worn.
Figure 14:
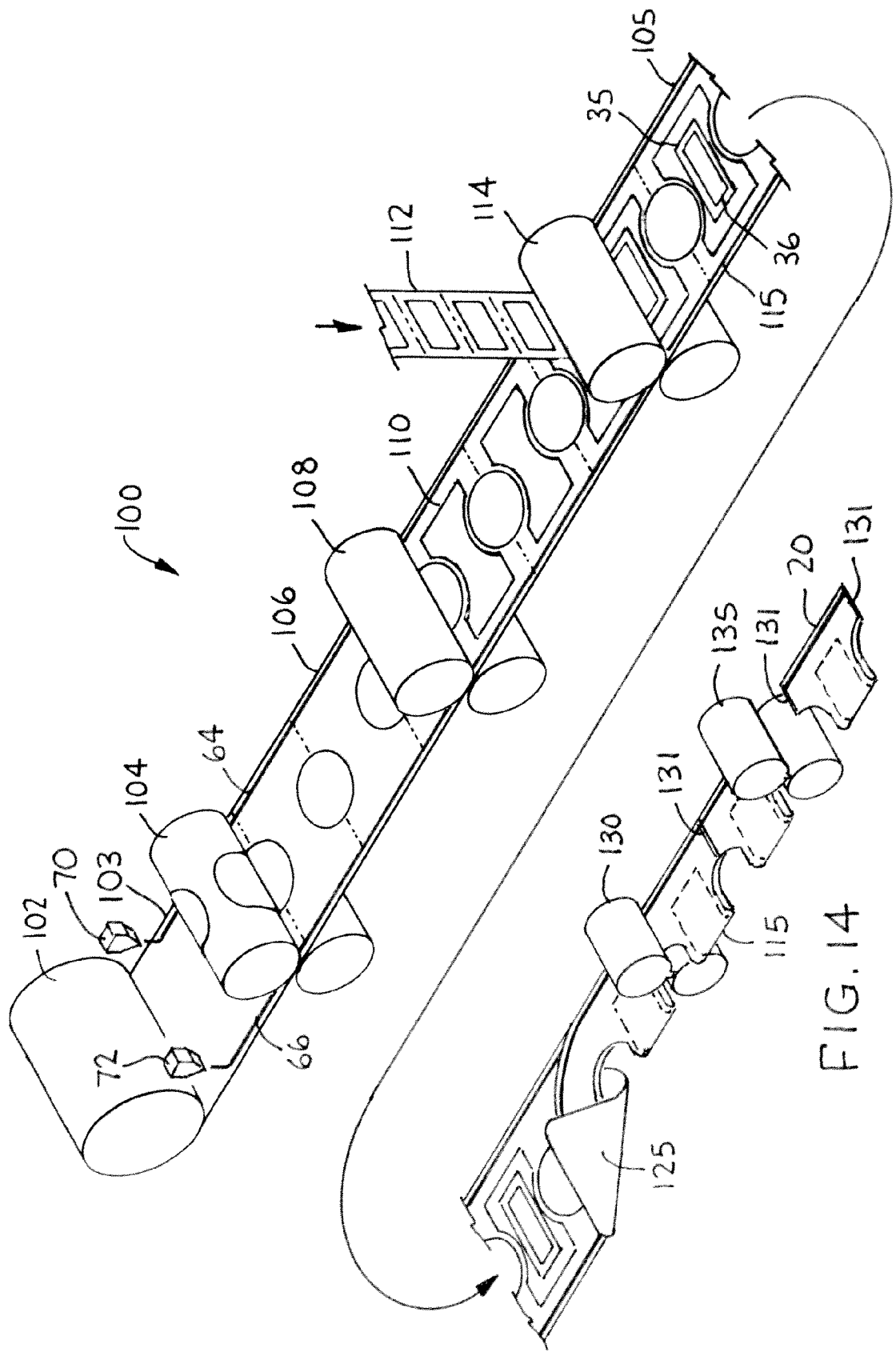
FIG. 14 representatively illustrates a perspective view of one embodiment of a manufacturing process incorporating principles of the process aspect of the present invention.

In one embodiment, the process further includes providing a crotch panel 30 positioned longitudinally between the front panel 22 and the back panel 26, wherein the front panel 22, the back panel 26, and the crotch panel 30 are continuous and integral with each other, as representatively illustrated in FIGS. 1, 2, and 12. One version of such an embodiment includes providing an hourglass shaped panel comprising an elastomeric film laminate. In particular embodiments, the laminate comprises two nonwoven layers superposed on opposing top and bottom surfaces of an elastomeric polymeric film such that the polymeric film is sandwiched between the two nonwoven facings, wherein both the polymeric film and both nonwoven layers extend substantially through the entire area of each laminate. Another version of such an embodiment includes providing an hourglass panel comprising a nonwoven substrate which is imparted with elastic properties by adhesively attaching elastic strands thereto. The strands and adhesive are, in particular embodiments, sandwiched to the hourglass panel with a second nonwoven layer or layers.

One technique, representatively illustrated in FIG. 17 as process 100, to generate a garment employing such an hourglass shaped panel is to begin with a roll supply 102 of an elastomeric film laminate web 103. After the laminate is unwound, trim portions are removed by a cutter 104 to define an interconnected series of hourglass shaped panels 106. In certain embodiments, the process 100 can further include deactivating a central region of each panel in the interconnected series 106 via a deactivation unit 108 to create deactivated regions 110 in the elastomeric film laminate web 103. The deactivation can be accomplished by any of a variety of means. Frequently, some form of energy is applied to deactivate the central region of each panel in the series, such as pressure, heat, ultrasonic energy, combinations thereof, and the like. Techniques employing pressure, heat, and ultrasonic energy are known in the art. The deactivation can occur in a variety of patterns. For example, the deactivating energy could be applied in a solid pattern, a series of vertical stripes, horizontal stripes, or diagonal stripes, a series of squares or dots, or other suitable pattern.

Figure 4:
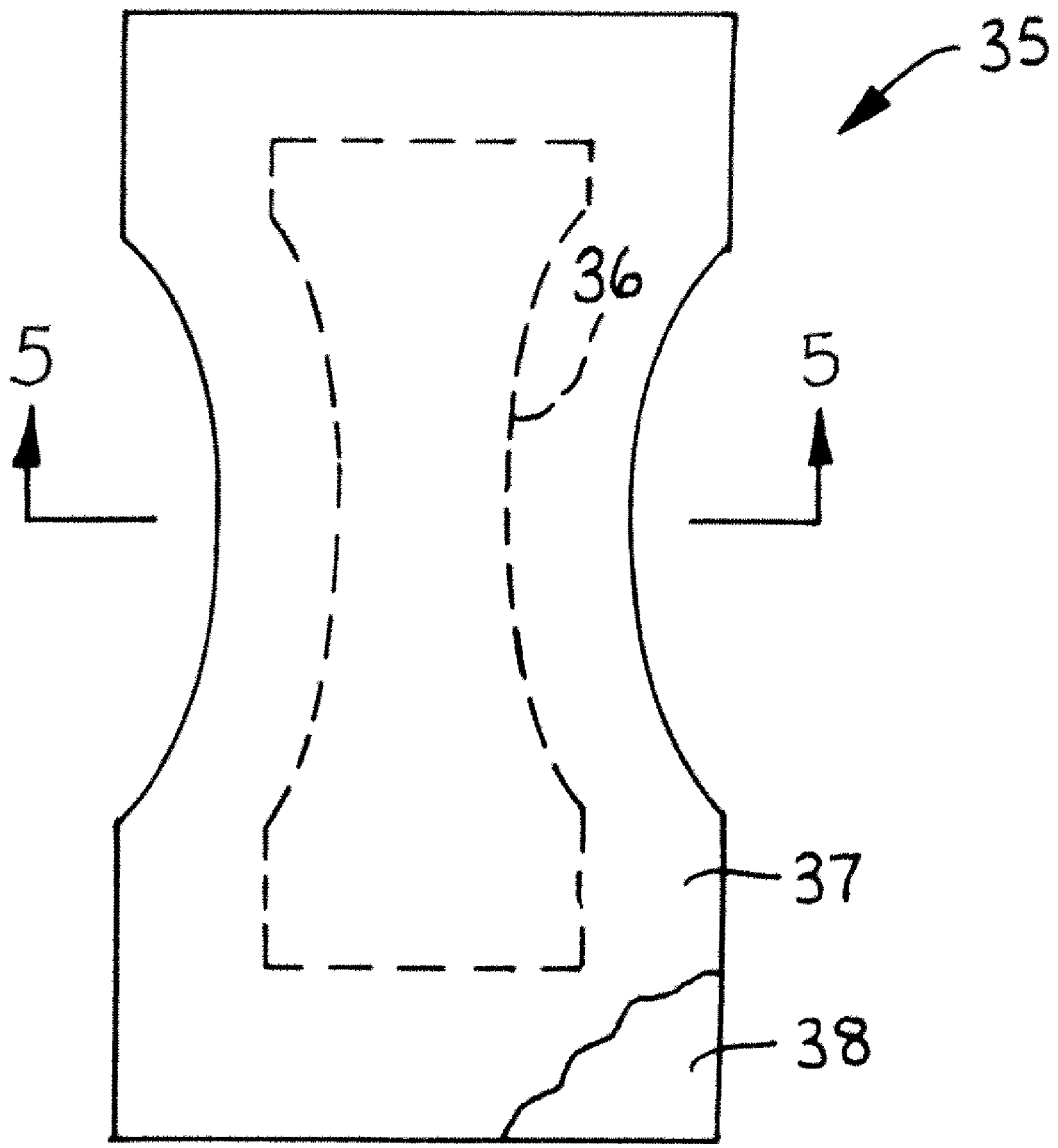
FIG. 4 representatively illustrates a plan view of an absorbent insert suitable for use in conjunction with the present invention, with portions cut away to show underlying features.
Figure 5:
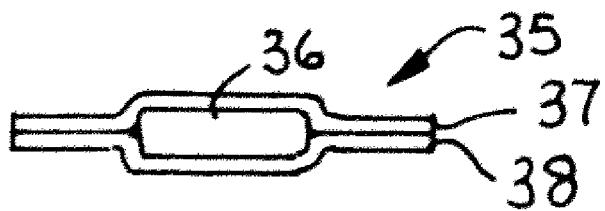
FIG. 5 representatively illustrates a cross-sectional view taken along line 5-5 in FIG. 4.

The process 100 further includes providing an absorbent insert 35. The insert comprises an absorbent member 36. One example of a suitable insert 35 comprises a liquid-permeable bodyside liner 37, a garment-side liquid-impermeable backsheet 38, and an absorbent member 36 comprised of wood pulp fluff and superabsorbent polymer (FIGS. 4 and 5). In particular embodiments, each of these components is introduced into the process in continuous fashion, resulting in an interconnected series 112 of absorbent inserts 35 that is fed into the rest of the process 100, such as is representatively illustrated in FIG. 14. Techniques to assemble an interconnected series 112 of absorbent inserts 35, such by sandwiching an absorbent member 36 between liner and backsheet layers, or by providing a thin, integral absorbent in roll form, such as an absorbent foam, are known in the art and are therefore not shown or discussed in detail herein.

The process 100 further includes attaching each absorbent insert 35 to an hourglass-shaped panel 105. For example, the absorbent insert can be attached to the panel at an attachment station 114, at which each absorbent insert is cut from the interconnected series 112 and applied to each panel 105 in the interconnected series of panels 112. The absorbent insert is attached to and extends between the front panel 22 and the back panel 26 (FIGS. 1 and 12). In certain embodiments in which a deactivated region 110 has been created, a portion of the absorbent member 36 overlaps at least a portion of the deactivated region 110.

Figure 15:
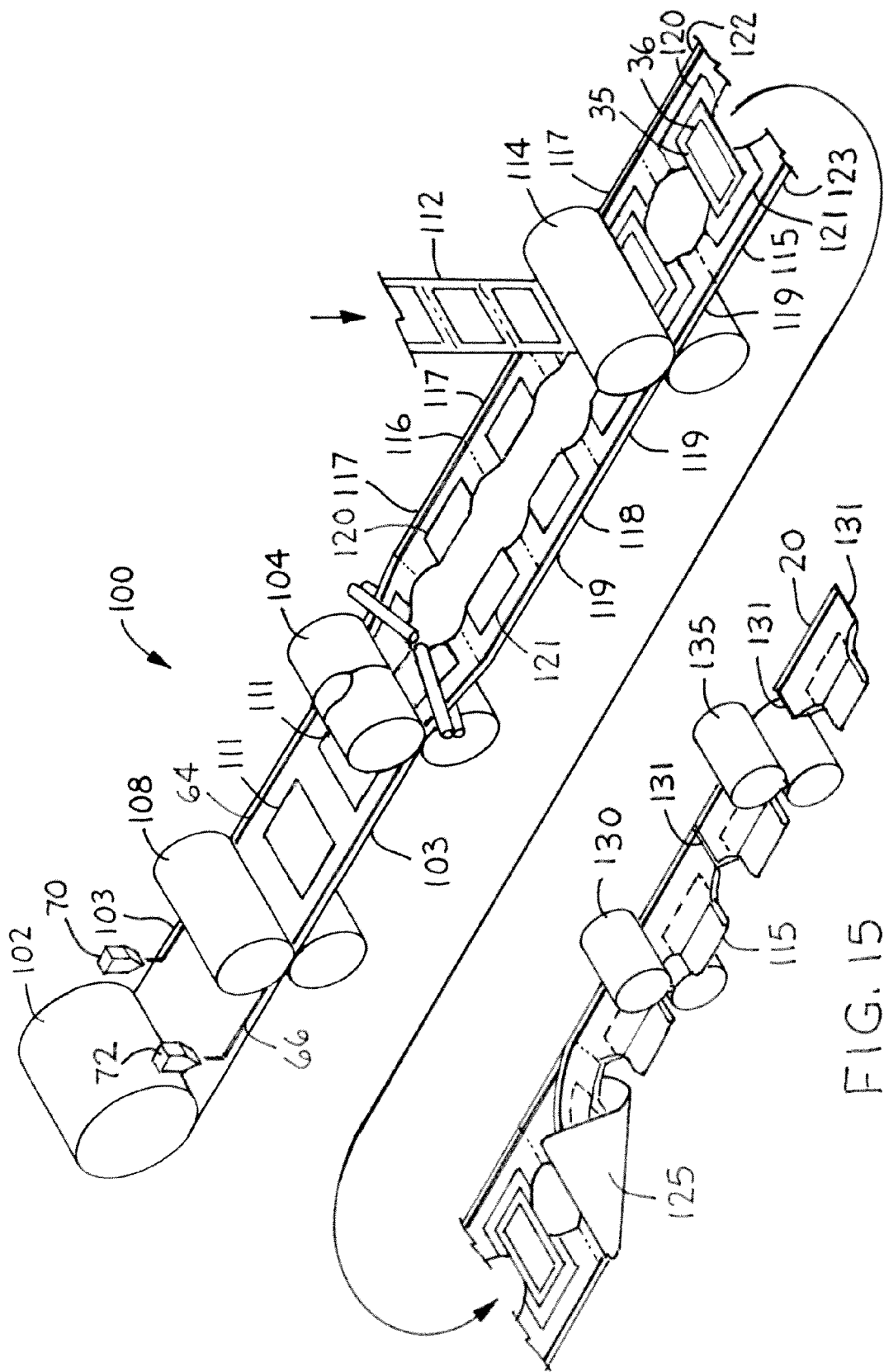
FIG. 15 representatively illustrates a perspective view of an alternative embodiment of a manufacturing process incorporating principles of the process aspect of the present invention.

An alternative configuration of the process aspect of the present invention, representatively illustrated in FIG. 15, includes providing a front panel comprising an elastomeric film laminate and defining a waist edge and a crotch edge, and providing a back panel comprising an elastomeric film laminate and defining a waist edge and a crotch edge. For example, a roll 102 of an elastomeric film laminate web 103 is unwound. The process 100 can include deactivating regions 111 of the laminate web 103 via a deactivation unit 108 to create deactivated regions 111 in the elastomeric film laminate web 103. Any of the deactivation techniques and patterns described above would be suitable to perform the deactivation in this embodiment (deactivation is, as with the embodiment of FIG. 14, optional). Additionally, the laminate web 103 is shaped and slit into two separate webs 116/118 via a cutter 104; namely, the web 103 is split into a front panel web 116 defining an interconnected series of front panels 117 (each having a front panel deactivated region 120) and a back panel web 118 defining an interconnected series of back panels 119 (each having a back panel deactivated region 121). An absorbent insert 35 comprising an absorbent member 36 (such as described earlier) is provided and is attached to each front panel 122 and each back panel 123 at attachment station 114, such that the absorbent insert 35 extends between the front panel 122 and the back panel 123, and such that (in particular embodiments) a front portion of the absorbent member overlaps at least a portion of the front panel deactivated region 120, and such that a back portion of the absorbent member overlaps at least a portion of the back panel deactivated region 121. (In certain embodiments, the front panel web 116 and the back panel web 118 can be provided separately, as opposed to originating in a single parent roll.)

The process aspect of the invention further includes joining the first and second front side edges 24/25 to the first and second back side edges 28/29, such that the garment assumes a pull-on configuration. FIGS. 17 and 18 depict this joining action by way of folding the composite web 115 at a folding station 125, and subsequently bonding the front side edges 24/25 to the back side edges 28/29 at a side bonding station 130. (The term "edges" can refer either to an area where a component, such as a panel, physically terminates, or to the region of transition from one panel to the next on an interconnected series of components, such as an interconnected series of hourglass panels 106, an interconnected series of front panels 117, or on an interconnected series of back panels 119. Thus, FIGS. 17 and 18 depict the joining of first and second front side edges 24/25 to first and second back side edges 28/29 by way of the folding station 125 and the side bonding station 130.) The composite web 115 is cut into individual garments 20 at cutting stating 135. The cutting can occur after the bonding step (as depicted in FIGS. 17 and 18), or the cutting and bonding steps can occur simultaneously at a single station.

Figure 6:
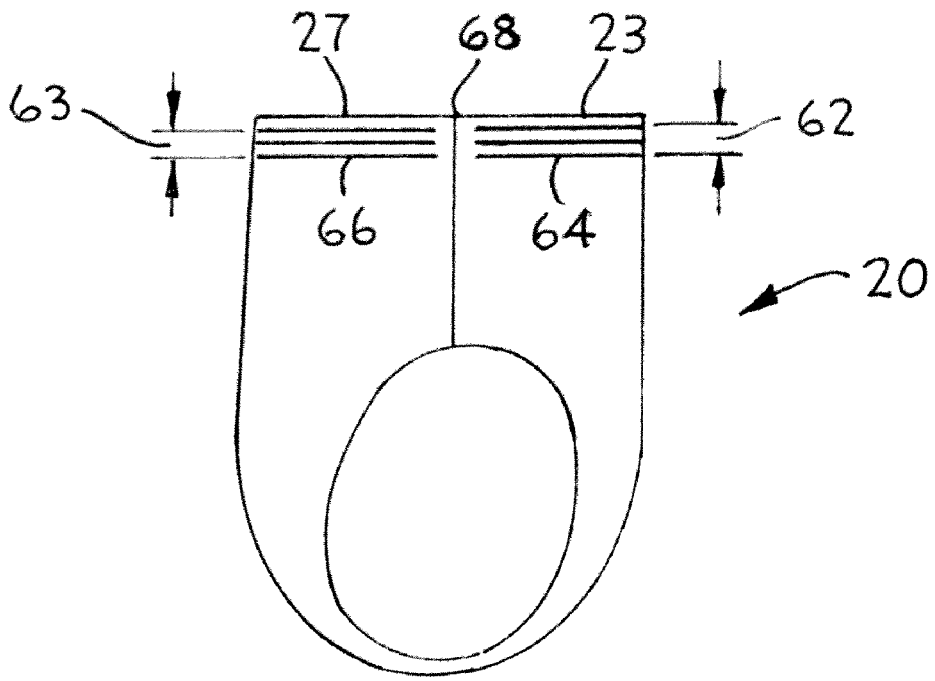
FIG. 6 representatively illustrates a side view of one embodiment of an absorbent garment incorporating principles of the garment aspect of the present invention, with the absorbent garment in its fully assembled configuration.
Figure 7:
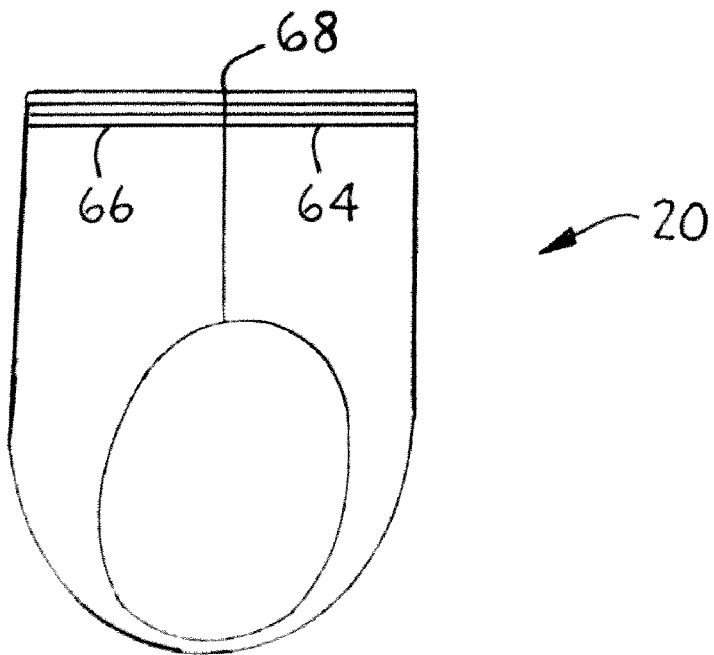
FIG. 7 representatively illustrates a side view of an alternative embodiment of an absorbent garment incorporating principles of the garment aspect of the present invention, with the absorbent garment in its fully assembled configuration.
Figure 8:
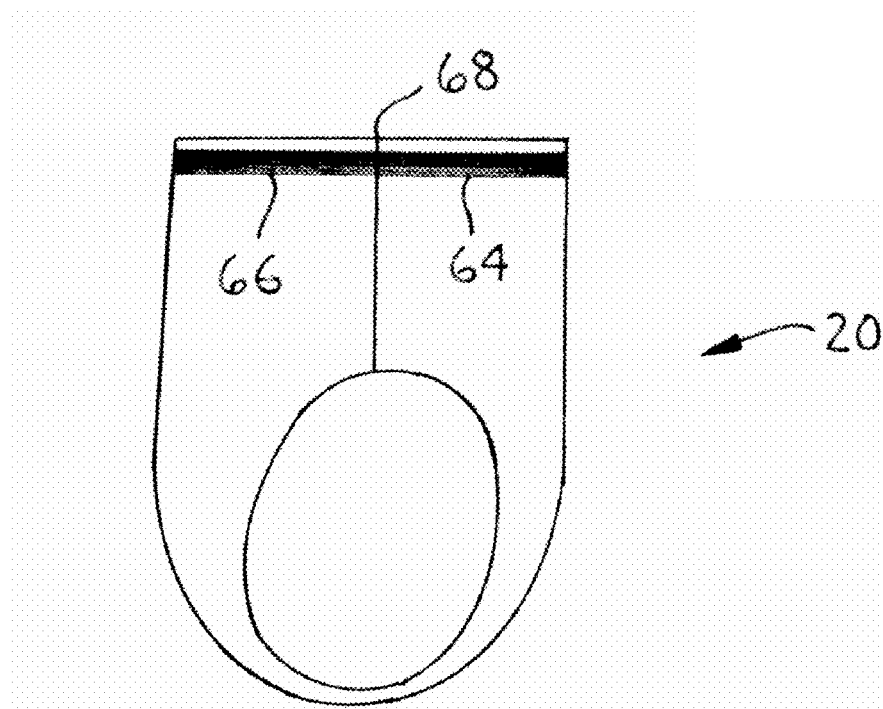
FIG. 8 representatively illustrates a side view of an alternative embodiment of an absorbent garment incorporating principles of the garment aspect of the present invention, with the absorbent garment in its fully assembled configuration.
Figure 9:
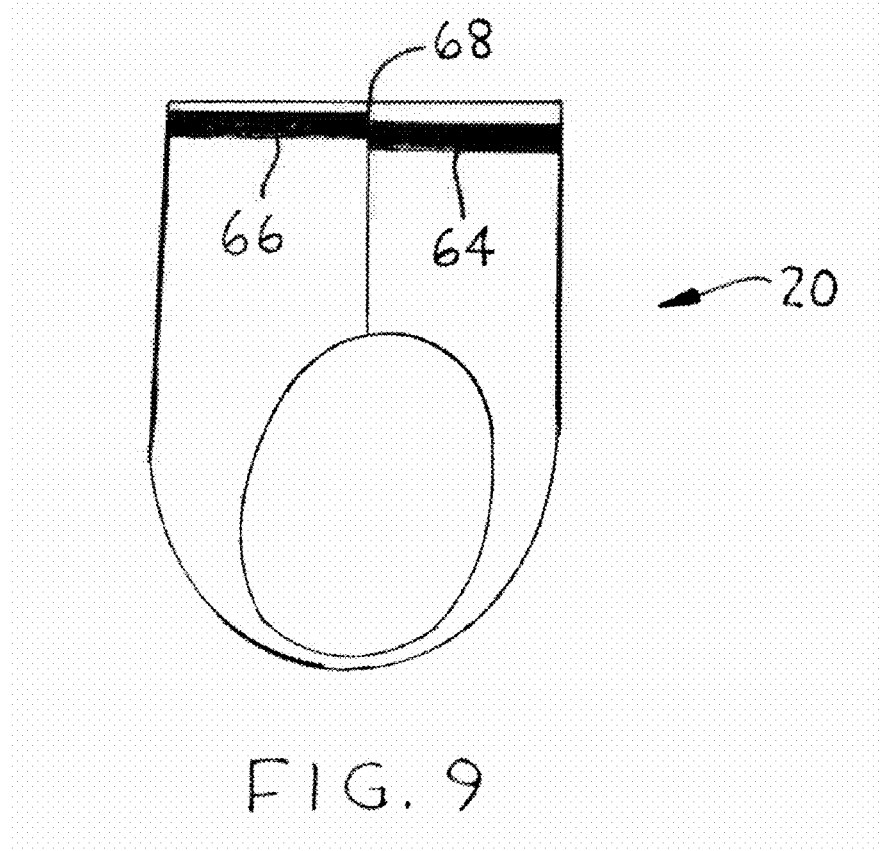
FIG. 9 representatively illustrates a side view of an alternative embodiment of an absorbent garment incorporating principles of the garment aspect of the present invention, with the absorbent garment in its fully assembled configuration.
Figure 10:
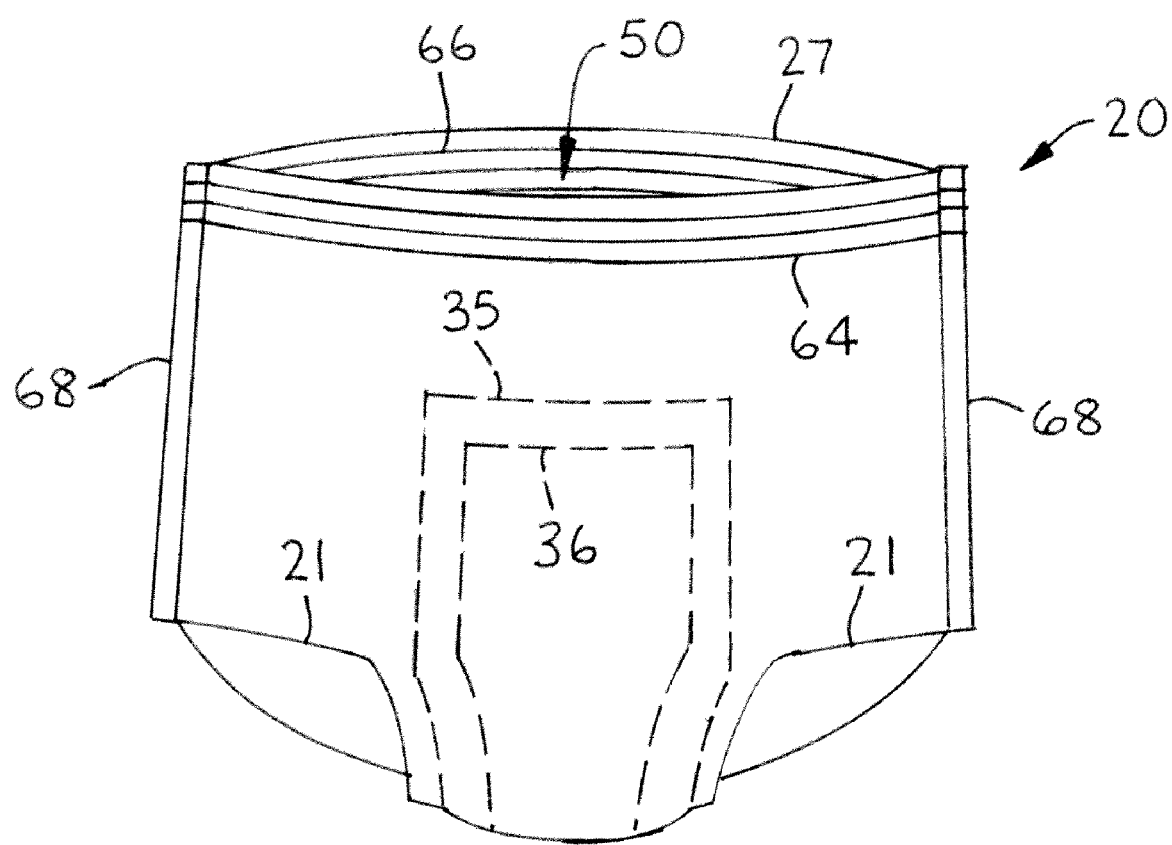
FIG. 10 representatively illustrates a front perspective view of the embodiment of FIG. 7, with the front and back waist regions being joined such that the garment is in its fully assembled, pant-like configuration.
Figure 11:
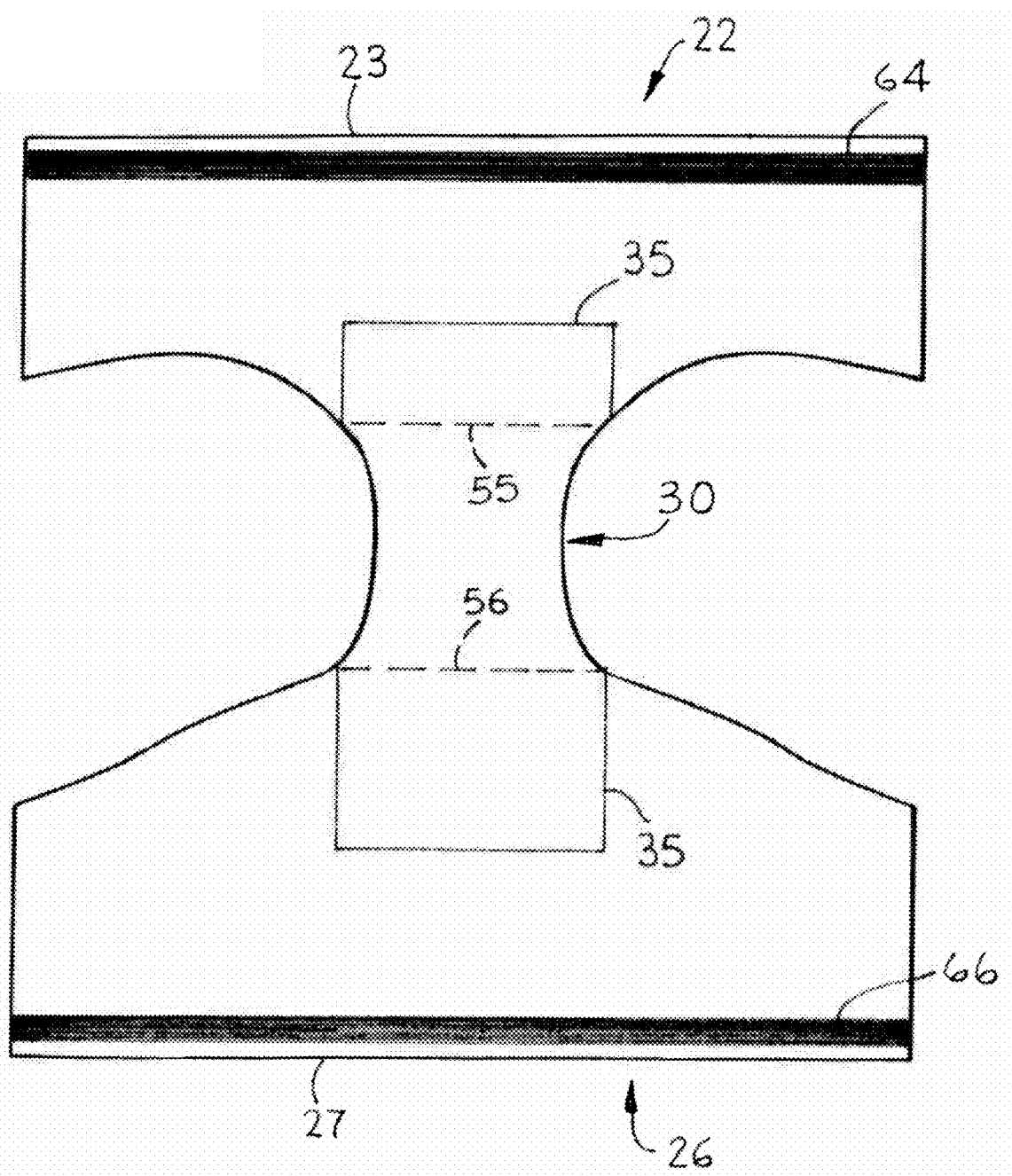
FIG. 11 representatively illustrates a plan view of an alternative embodiment of an absorbent garment incorporating principles of the garment aspect of the present invention in a longitudinally stretched and laid-flat condition, prior to the joining of the front and back waist regions, showing the surface of the article that faces the wearer when the article is worn, but without an absorbent insert.

The process aspect of the present invention further includes printing a front waistband graphic 64 (such as at a first print station 70) on the front panel 22 proximate the front waist edge 23, such that the front waistband graphic 64 extends at least 90% of the front panel width 34. The process aspect further includes printing a back waistband graphic 66 (such as at a second print station 72) on the back panel 26 proximate the back waist edge 27, such that the back waistband graphic 66 extends at least 90% of the back panel width 52. For example, FIGS. 2 and 6 depict a front waistband graphic 64 that extends approximately 90% of the front panel width 34, and a back waistband graphic 66 that extends approximately 90% of the back panel width 52. In another embodiment, the front waistband graphic 64 extends from about 90% to about 98% of the front panel width 34, and the back waistband graphic 66 extends from about 90% to about 98% of the back panel width 52. One potential advantage of such a configuration is that by not extending a waistband graphic all the way to the side edges of the front or back panels (that is, by not extending the graphic 100% of the front or back panel widths), the graphic may in certain embodiments be less likely to affect the quality of the side bond 131 (e.g., the composition of the ink or other print fluid can affect the quality of the side bond in the bond region where the graphic is present).

In still another embodiment, the front waistband graphic extends 100% of the front panel width, and the back waistband graphic extends 100% of the back panel width, as representatively illustrated in FIG. 1. One potential advantage of such an embodiment is that after the front panel 22 and back panel 26 are joined together to define a pant-like garment, the front waistband graphic 64 and the back waistband graphic 66 can partially or completely align with one another to create to the appearance of a continuous, fully encircling waistband graphic, which imparts a more real, cloth underwear-like appearance to the absorbent garment 20. This is because in this particular embodiment, the front waistband graphic 64 and the back waistband graphic 66 abut each other at the side seams 68 of the garment 20, and together create the appearance of a unitary, continuous waistband.

Particular embodiments of the process aspect of the invention further comprises applying at least one front elastic member to the front panel such that the elastic member extends at least 90% of the front panel width in the final product (post cutting station 135) and that overlaps the front waistband graphic, and further comprises applying at least one back elastic member to the back panel such that the elastic member extends at least 90% of the back panel width in the final product (post cutting station 135) and that overlaps the back waistband graphic. One representative example of such an embodiment is illustrated in FIG. 1, which depicts three front elastic members 65 and three back elastic members 67. One potential advantage to having the elastic members overlap the front and back waistband graphics 64 and 66 is that in such an embodiment, the elastic members 65 and 67 can impart gathers to the front and back panels 22 and 26 in the region where the front waistband graphic 64 and back waistband graphic 66 are printed, which imparts a more real underwear-like appearance to the absorbent garment 20. Another embodiment comprises applying at least one front elastic member to the front panel such that the elastic member extends from about 90% to about 98% of the front panel width and overlaps the front waistband graphic, and further comprises applying at least one back elastic member to the back panel such that the elastic member extends from about 90% to about 98% of the back panel width and overlaps the back waistband graphic. One potential advantage of such a configuration is that by not extending the elastic members 65 and 67 all the way to the side edges of the front or back panels (that is, by not extending the elastic members 100% of the front or back panel widths), the elastic members will be less likely in certain embodiments to affect the quality of the side bond 131 (e.g., the composition and/or bulk of the elastic members can affect the quality of the side bond if the elastic members are present in the side bond region). Other embodiments of the process aspect of the invention comprise applying at least one front elastic member (such as, for example, two, three or four elastic members) to the front panel such that the elastic member extends 100% of the front panel width and overlaps the front waistband graphic, and further comprises applying at least one back elastic member (such as, for example, two, three, or four elastic members) to the back panel such that the elastic member extends 100% of the back panel width and overlaps the back waistband graphic.

The garment defines a longitudinal direction 32 which extends from the front waist edge 23 to the back waist edge 27, and a transverse direction 33 which is perpendicular to the longitudinal direction 32 and which extends from the first front side edge 24 to the second front side edge (and from the first back side edge 28 to the second back side edge 29). The front waistband graphic 64 defines a front waistband graphic width 62, which is the distance between two imaginary straight lines that extend transversely along the points or portions of the front waistband graphic 64 longitudinally nearest and longitudinally furthest from the front waist edge 23, respectively. The back waistband graphic 66 defines a back waistband graphic width 63, which is the distance between two imaginary straight lines that extend transversely along the points or portions of the back waistband graphic 66 longitudinally nearest and longitudinally furthest from the back waist edge 27, respectively. Widths should be measured when the garment is in a laid-flat, open, and fully extended condition. The graphics 64 and/or 66 can be printed on an external surface of the panels 22 and 26, or on an internal surface of the panels 22 and 26.

In particular embodiments, after the front panel 22 is joined to the back panel 26 to impart a pant-like configuration to the garment 20, the front waistband graphic 64 is in complete alignment with the back waistband graphic 66. As used herein, "complete alignment" means that the front waistband graphic width 62 is the same as the back waistband graphic width 63, and further that the front waistband graphic 64 and the back waistband graphic 66 have no longitudinal offset from each other in the assembled pant-like configuration, as representatively illustrated in FIGS. 6, 7, and 8.

In other embodiments, after the front panel 22 is joined to the back panel 26 to impart a pant-like configuration to the garment 20, the front waistband graphic 64 is in substantial alignment with the back waistband graphic 66. As used herein, "substantial alignment" means either that the front waistband graphic width 62 is not the same as the back waistband graphic width 63, or that the front waistband graphic width 62 is the same as the back waistband graphic width 63 but that the front waistband graphic 64 and the back waistband graphic 66 are longitudinally offset from each other in the assembled pant-like configuration from between 1% and 20% of the front waistband graphic width 62, as representatively illustrated in FIG. 9.

In particular embodiments, the front waistband graphic 64 comprises a single transversely extending stripe, as representatively illustrated in FIGS. 1, 2, 8, and 9. In other embodiments, the front waistband graphic 64 comprises at least two transversely extending stripes (such as, for example, two, three, four, or five stripes) as representatively illustrated in FIGS. 2, 6, and 7. In particular embodiments, the back waistband graphic 66 comprises a single transversely extending stripe, as representatively illustrated in FIGS. 1, 2, 8, and 9. In other embodiments, the back waistband graphic 66 comprises at least two transversely extending stripes (such as, for example, two, three, four, or five stripes), as representatively illustrated in FIGS. 2, 6, and 7. In desirable embodiments, the front waistband graphic 64 and the back waistband graphic 66 each have a matching number of stripes, and the stripes match in width, as representatively illustrated in FIGS. 1, 2, 6, 7, and 8.

In particular embodiments, the side seams 68 of the garment 20 are permanently bonded, non-refastenable side seams. For example, in particular embodiments of the process aspect of the present invention, the joining of the first and second front side edges to the first and second back side edges creates a pair of permanently bonded, non-refastenable side seams. In other embodiments, the side seams 68 are releasable and refastenable. For example, in particular embodiments of the process aspect of the present invention, the joining of the first and second front side edges to the first and second back side edges creates a pair of releasable and refastenable seams.

In particular embodiments of both the process and product aspect of the present invention, the front panel 22 defines a front crotch edge 55 longitudinally opposite the front waist edge 23, and the back panel 26 defines a back crotch edge 56 longitudinally opposite the back waist edge 27, and the front crotch edge 55 is longitudinally spaced apart from the back crotch edge 56 such that the front panel 22 and the back panel 26 are separate from and non-integral with each other. An example of such a "3-piece" configuration (the three primary pieces of the garment being the front panel 22, the back panel 26, and the crotch panel 30) is representatively illustrated in FIGS. 11 and 13. In such an embodiment, the absorbent insert 35 can but need not function as the crotch panel 30.

In particular embodiments of the process aspect of the invention, providing the front panel comprises providing a front upper panel 46 and a front lower panel 47, and connecting the front upper panel 46 to the front lower panel 47 along seam 53, such that the front upper panel is proximate the front waist edge 23 and the front lower panel 47 is proximate the front leg edges 21. Furthermore, in these particular embodiments, providing the back panel 26 comprises providing a back upper panel 48 and a back lower panel 49, and connecting the back upper panel 48 to the back lower panel 49 along seam 54, such that the back upper panel 48 is proximate the back waist edge 27 and the back lower panel 49 is proximate the back leg edges 45. Furthermore, in these particular embodiments, printing the front waistband graphic 64 on the front panel 22 proximate the front waist edge 23 comprises printing the front waistband graphic 64 on the front upper panel 46, and printing the back waistband graphic 66 on the back panel 26 proximate the back waist edge 27 comprises printing the back waistband graphic 66 on the back upper panel 48. Such a configuration is representatively illustrated in FIGS. 12 and 13. In particular embodiments, the front upper panel 46 includes at least one elastic strand, and the front lower panel 47 includes an elastomeric film, and the back upper panel 48 includes at least one elastic strand, and the back lower panel 49 includes an elastomeric film.

As representatively illustrated in FIGS. 17 and 18, certain commercial embodiments of the process aspect of the present invention comprise printing an interconnected series of front waistband graphics on the interconnected series of front panels 22, and printing an interconnected series of back waistband graphics on the interconnected series of back panels 26. One embodiment comprises printing an interconnected series of front waistband graphics on an interconnected series of front upper panels 46, and printing an interconnected series of back waistband graphics on an interconnected series of back upper panels 48.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A process for making a pant-like disposable absorbent garment comprising:
   providing a front panel, the front panel defining a front waist edge, first and second front leg edges, opposing first and second front side edges which extend from the front waist edge to the first and second front leg edges, and a front panel width which extends from the first front side edge to the second front side edge at the front waist edge;
   providing a back panel, the back panel defining a back waist edge, first and second back leg edges, opposing first and second back side edges which extend from the back waist edge to the first and second back leg edges, and a back panel width which extends from the first back side edge to the second back side edge at the back waist edge;
   attaching an absorbent insert to the front panel and to the back panel, such that the absorbent insert extends between and connects the front panel to the back panel;
   printing a front waistband graphic on the front panel proximate the front waist edge, such that the front waistband graphic extends at least 90% of the front panel width;
   printing a back waistband graphic on the back panel proximate the back waist edge, such that the back waistband graphic extends at least 90% of the back panel width; and
   joining the first and second front side edges to the first and second back side edges, such that the garment assumes a pull-on configuration, and such that the front waistband graphic is in at least substantial alignment with the back waistband graphic,
   wherein providing the front panel comprises providing a front upper panel and a front lower panel, connecting the front upper panel to the front lower panel, such that the front upper panel is proximate the front waist edge and the front lower panel is proximate the front leg edges; and wherein providing the back panel comprises providing a back upper panel and a back lower panel, connecting the back upper panel to the back lower panel, such that the back upper panel is proximate the back waist edge and the back lower panel is proximate the back leg edges;
   wherein printing the front waistband graphic on the front panel proximate the front waist edge comprises printing the front waistband graphic on the front upper panel, and wherein printing the back waistband graphic on the back panel proximate the back waist edge comprises printing the back waistband graphic on the back upper panel.

2. The process of claim 1 further comprising applying at least one front elastic member to the front panel such that the elastic member extends at least 90% of the front panel width and overlaps the front waistband graphic, and further comprises applying at least one back elastic member to the back panel such that the elastic member extends at least 90% of the back panel width and overlaps the back waistband graphic.

3. The process of claim 1 wherein the front waistband graphic extends 100% of the front panel width, and wherein the back waistband graphic extends 100% of the back panel width.

4. The process of claim 1 wherein the joining of the first and second front side edges to the first and second back side edges places the front waistband graphic in complete alignment with the back waistband graphic.

5. The process of claim 1 wherein the front waistband graphic comprises at least two transversely extending stripes, and wherein the back waist band graphic matches the front waistband graphic so as to have the same number and width of stripes.

6. The process of claim 1 further comprising providing a crotch panel positioned longitudinally between the front panel and the back panel, wherein the front panel, the back panel, and the crotch panel are continuous and integral with each other.

7. The process of claim 1 wherein the front panel defines a front crotch edge longitudinally opposite the front waist edge and wherein the back panel defines a back crotch edge longitudinally opposite the back waist edge, wherein the front crotch edge is longitudinally spaced apart from the back crotch edge such that the front panel and the back panel are separate from and non-integral with each other.

8. The process of claim 1, wherein the front upper panel includes at least one elastic strand, and wherein the front lower panel includes an elastomeric film, and further wherein the back upper panel includes at least one elastic strand, and wherein the back lower panel includes an elastomeric film.

9. The process of claim 1 further comprising providing an interconnected series of front panels and an interconnected series of back panels, and further comprising printing an interconnected series of front waistband graphics on the interconnected series of front panels, and printing an interconnected series of back waistband graphics on the interconnected series of back panels.

10. A pant-like disposable absorbent garment comprising:
   a front panel, the front panel defining a front waist edge, first and second front leg edges, opposing first and second front side edges which extend from the front waist edge to the first and second front leg edges, and a front panel width which extends from the first front side edge to the second front side edge at the front waist edge;
   a back panel, the back panel defining a back waist edge, first and second back leg edges, opposing first and second back side edges which extend from the back waist edge to the first and second back leg edges, and a back panel width which extends from the first back side edge to the second back side edge at the back waist edge, the first and second front side edges being joined to the first and second back side edges such that the garment defines a pull-on configuration;

an absorbent insert extending between and interconnecting the front panel to the back panel;

a front waistband graphic disposed on the front panel proximate the front waist edge, the front waistband graphic extending at least 90% of the front panel width;

a back waistband graphic disposed on the back panel proximate the back waist edge, the back waistband graphic extending at least 90% of the back panel width;

wherein the front waistband graphic is in at least substantial alignment with the back waistband graphic.

11. The garment of claim 10 further comprising at least one front elastic member disposed on the front panel such that the elastic member extends at least 90% of the front panel width and overlaps the front waistband graphic, and further comprising at least one back elastic member disposed on the back panel such that the elastic member extends at least 90% of the back panel width and overlaps the back waistband graphic.

12. The garment of claim 10 wherein the front waistband graphic extends 100% of the front panel width, and wherein the back waistband graphic extends 100% of the back panel width.

13. The garment of claim 12 wherein the garment defines a waist hoop, and wherein the front waistband graphic and the back waistband graphic together define a garment waistband graphic that extends around an entire circumference of the waist hoop.

14. The garment of claim 10 wherein the front waistband graphic is in complete alignment with the back waistband graphic.

15. The garment of claim 10 wherein the front waistband graphic comprises at least two transversely extending stripes, and wherein the back waist band graphic substantially matches the front waistband graphic so as to have the same number and width of stripes.

16. The garment of claim 10 further including a crotch panel positioned longitudinally between the front panel and the back panel, wherein the front panel, the back panel, and the crotch panel are continuous and integral with each other.

17. The garment of claim 10 wherein the front panel defines a front crotch edge longitudinally opposite the front waist edge and wherein the back panel defines a back crotch edge longitudinally opposite the back waist edge, wherein the front crotch edge is longitudinally spaced apart from the back crotch edge such that the front panel and the back panel are separate from and non-integral with each other.

18. The garment of claim 10 wherein the front panel comprises a front upper panel proximate the front waist edge and a front lower panel proximate the front leg edges, and wherein the back panel comprises a back upper panel proximate the back waist edge and a back lower panel proximate the back leg edges, wherein the front waistband graphic is disposed on the front upper panel, and wherein back waistband graphic is disposed on the back upper panel.

19. The garment of claim 18 wherein the front upper panel includes at least one elastic strand, and wherein the front lower panel includes an elastomeric film, and further wherein the back upper panel includes at least one elastic strand, and the back lower panel includes an elastomeric film.

* * * * *